(12) United States Patent
Wedenberg et al.

(10) Patent No.: US 12,076,586 B2
(45) Date of Patent: Sep. 3, 2024

(54) METHOD AND SYSTEM FOR ROBUST RADIOTHERAPY TREATMENT PLANNING FOR BIOLOGICAL UNCERTAINTIES

(71) Applicant: RaySearch Laboratories AB, Stockholm (SE)

(72) Inventors: Minna Wedenberg, Uppsala (SE); Jakob Ödén, Sollentuna (SE); Albin Fredriksson, Stockholm (SE); Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 408 days.

(21) Appl. No.: 17/618,088

(22) PCT Filed: Jun. 2, 2020

(86) PCT No.: PCT/EP2020/065172
§ 371 (c)(1),
(2) Date: Dec. 10, 2021

(87) PCT Pub. No.: WO2020/249419
PCT Pub. Date: Dec. 17, 2020

(65) Prior Publication Data
US 2022/0296925 A1 Sep. 22, 2022

(30) Foreign Application Priority Data
Jun. 11, 2019 (EP) .................................... 19179427

(51) Int. Cl.
*A61N 5/10* (2006.01)
(52) U.S. Cl.
CPC ......... *A61N 5/1031* (2013.01); *A61N 5/1038* (2013.01); *A61N 2005/1041* (2013.01)

(58) Field of Classification Search
CPC ................ A61N 5/1031; A61N 5/1038; A61N 2005/1041
See application file for complete search history.

(56) References Cited

U.S. PATENT DOCUMENTS

| 6,411,675 B1 | 6/2002 | Llacer |
| 2012/0136194 A1 | 5/2012 | Zhang et al. |

(Continued)

FOREIGN PATENT DOCUMENTS

| EP | 2 878 338 A1 | 6/2015 |
| EP | 3 228 356 A1 | 10/2017 |

(Continued)

OTHER PUBLICATIONS

Fredriksson et al., "A Critical Evaluation of Worst Case Optimization Methods for Robust Intensity-Modulated Proton Therapy Planning," Medical Physics, vol. 41, No. 8, pp. 081701-1 to 081701-11, 2014.

(Continued)

*Primary Examiner* — Mark R Gaworecki
(74) *Attorney, Agent, or Firm* — Faegre Drinker Biddle & Reath LLP

(57) ABSTRACT

A method for generating a robust radiotherapy treatment plan for a treatment volume of a subject, the treatment volume being defined using a plurality of voxels, the method comprising the steps of defining (S100) an optimization problem using at least one optimization function for a biological endpoint related to the radiotherapy treatment; defining (S102) a set of scenarios comprising at least a first scenario and a second scenario, wherein at least two of the scenarios in the set of scenarios represent different biological models to quantify the same biological endpoint; calculating (S104) an optimization function value for each scenario in the set of scenarios; generating (S106) a (Continued)

radiotherapy treatment plan by robustly optimizing the optimization function value evaluated over the set of scenarios.

11 Claims, 2 Drawing Sheets

(56) References Cited

U.S. PATENT DOCUMENTS

| | | | |
|---|---|---|---|
| 2017/0014642 A1* | 1/2017 | An | A61N 5/1084 |
| 2018/0117357 A1 | 5/2018 | Fredriksson et al. | |

FOREIGN PATENT DOCUMENTS

| | | | | |
|---|---|---|---|---|
| JP | 2007-531556 A | 11/2007 | | |
| JP | 2012-506724 A | 3/2012 | | |
| JP | 2012-521792 A | 9/2012 | | |
| JP | 2013-529481 A | 7/2013 | | |
| JP | 2016-520385 A | 7/2016 | | |
| JP | 2016-532530 A | 10/2016 | | |
| JP | 2017-514532 A | 6/2017 | | |
| JP | 2019-510585 A | 4/2019 | | |
| WO | WO-2012024448 A2 * | 2/2012 | | A61N 5/103 |
| WO | WO-2015080647 A1 * | 6/2015 | | A61N 5/1031 |
| WO | WO-2019160571 A1 * | 8/2019 | | A61N 5/1031 |

OTHER PUBLICATIONS

Fredriksson, "A Characterization of Robust Radiation Therapy Treatment Planning Methods—from Expected Value to Worst Case Optimization," Medical Physics, No. 39, vol. 8, pp. 5169-5181, 2012.

* cited by examiner

METHOD AND SYSTEM FOR ROBUST RADIOTHERAPY TREATMENT PLANNING FOR BIOLOGICAL UNCERTAINTIES

CROSS REFERENCE TO RELATED APPLICATIONS

This application is a National Stage of International Application No. PCT/EP2020/065172, filed Jun. 2, 2020, and claims the benefit of European Patent Application No. 19179427.0, filed Jun. 11, 2019, the entire contents of each of which are incorporated herein by reference.

TECHNICAL FIELD

The present disclosure relates in general to the field of radiotherapy treatment, in particular, the generation, optimization, and evaluation of a radiotherapy treatment plan.

BACKGROUND ART

Cancer is a widespread disease that expresses itself through the errant growth of abnormal cells. If the uncontrolled growth of these cells is not stopped, it can be fatal. The fatal trend of cancer worldwide is steadily increasing along with the overall estimated cost for cancer management. This has led to an increased demand from the public to develop more effective tools and technologies for treating and curing the disease. With the rapid advancement of medical imaging, tumors are being diagnosed in early stages when they still are local or regional. Different kinds of radiotherapy, including brachytherapy and particle therapy, surgery and systemic therapies including chemotherapy, are effective in treating local cancer cells, or tumors.

Radiotherapy is a modality of cancer treatment that uses ionizing radiation that damages the DNA and causes cell death within the region being irradiated. The main goal of radiotherapy is to eradicate the cancer cells by delivering a radiation dose high enough to kill all the targeted tumor cells while simultaneously avoiding unacceptable injury to healthy structures. The physical quantity of the impaired energy per unit mass, the so-called absorbed dose, is expressed in units of Gray (Gy), according to the International System of Units (SI), where one Gy equals one Joule of energy absorbed per kilogram of matter.

Modern radiotherapy treatment planning typically involves the following set of steps: patient imaging, target definition (i.e., structure contouring), dose prescription, machine and particle type selection, parameter definition, beam configuration selection, plan generation (often in the form of plan optimization), and quality assurance and/or quality control.

In the field of radiotherapy treatment planning, treatment planners can generate different types of radiotherapy treatment plans for external radiotherapy treatment. In order to generate a treatment plan, the specialist needs to identify the region to be treated in the patient's body and assess organs-at-risk (OAR) using conventional scanning techniques like computer tomography (CT). The target volume is then defined as the volume within a patient's body that is affected by a tumor, for example, a prostate. Studies have shown that the quality of a treatment plan is closely linked to the experience of the person performing the treatment, quality of the imaging devices and treatment devices, as well as many technical parameters like beam quality. This suggests that many treatment plans have room for improvement, especially if the treatment plan was prepared by less experienced personnel. Moreover, the use of inadequate planning methods, early termination of the optimization process, or measuring plan quality in an inadequate way, as well as misinterpretation of the parameters' weight can be a significant detriment to treatment quality.

Once the regions to be treated are imaged, physicians contour the tumor and OAR as well as prescribe the desired dose to treat the tumor. Thereafter, medical physicists start to work on the plan generation and generate the plan with one or multiple fields and beams for treating the patient. A large number of human work hours are being spent on plan optimization and quality control to minimize the detrimental effects on the surrounding tissues and increase the plan effectiveness. This suggests additional expenses to the hospital, the society and creates challenges of delivering radiotherapy treatment on time.

Radiotherapy can use e.g. high energy photons (X-rays) or beams of protons or heavier ions like helium or carbon. Every radiation type has its own characteristic distribution of energy depositions in matter which affects the physical, chemical and biological effects. For photons, cell damage is proportional to the absorbed energy (=dose). For protons and heavier ions, cell damage, in addition, depends on the distribution of absorbed energy events characterized e.g. with ionization density per particle along the ion track. The ionization density depends on, inter alia, the energy of the particle. The ionization density is often quantified in terms of linear energy transfer (LET) i.e. energy loss per distance (common units areMeV/cm or keV/µm). The LET is for example low at high proton energy. The LET increases towards lower proton energy, reaches a maximum and then decreases. The LET maximum is reached when the residual range of the proton is small and hence occurs in the Bragg peak.

Since there is a need to kill the tumor cells as effectively as possible, high LET portions are desirable inside the tumor. In healthy tissue outside of the tumor it desirable to have as low dose and low LET as possible.

Absorbed dose and spatial distribution of energy depositions are important quantities for the biological effect of radiation. However, there are many factors affecting the biological response including the inherent radiosensitivity of the biological system (cell, tissue, organ, etc.), the degree of oxygenation, the dose distribution within the irradiated volume, and the dose fractionation schedule (dose per fraction, time between fractions, overall treatment time, etc.).

The aim of curative radiotherapy is to obtain local tumor control with high probability without a too high risk of unacceptable side effects. However, in treatment planning, the clinical goals are instead often stated in terms of physical quantities such as prescription doses to the target, and dose-volume limits to regions of interest, and the quality of a radiotherapy plan is usually judged by its dose conformity, fulfillment of physical clinical goals, and treatment delivery time. The dose conformity describes how well the high radiation dose region conforms to the targeted tumor and spares the surrounding healthy tissue, while treatment delivery time describes how long treatment takes and the efficiency of the treatment machines used.

These physical quantities are surrogates of biological outcome for the patients used instead of estimating the probability of cure and side effects directly. Mathematical radiobiological models aim to bridge this gap by explicitly estimating the tumor control probability (TCP) and the normal tissue complication probability (NTCP) so that the desired dose distribution is determined based on the radiosensitivity of the tumor(s) and organ(s) at risk. Generally, radiobiological models can be used to e.g. describe the relation between physical quantities of radiation and biological effect, to interpolate and extrapolate from known outcomes, estimate the outcome of a new treatment technique, compensate for treatment interruptions, overdosage or underdosage, and assist in decision making. Instead of estimating the outcome directly, biological models have in practice often been used to convert non-standard dose distribution to traditional dose distributions. Large experience of the relationship between absorbed dose and clinical outcome has been gained from the long use of treatments with uniform intensity photon beams with fraction doses around 2 Gy. To take advantage of this experience given new treatment techniques, biological models has been used to convert proton and ion doses into equivalent photon doses using a factor for the relative biological effectiveness (RBE-models), inhomogeneous dose distributions to equivalent uniform distributions (EUD-models), and special fractionation schedules into equivalent standard fraction doses (EQD-models and BED-models). These models can be used in plan optimization and evaluation to include biological aspects.

The standard in proton and ion therapy treatment planning is to scale the absorbed physical dose with RBE-factors obtained with some RBE-model to obtain the corresponding dose distributions of a reference radiation quality, often a photon energy spectrum, with the same level of biological damage. In proton therapy, a simple scaling of the absorbed dose with a constant RBE factor equal to 1.1 is clinical standard. The range uncertainty due to increased RBE at the end of the proton range (together with other range uncertainties), is instead indirectly handled through the choice of beam angles and margins. Other RBE-models, not yet used clinically as of today, aim to estimate the RBE more accurately by including factors that affect the proton RBE such as the LET, dose per fraction, cell type/tissue type, and the biological endpoint. There are active discussions about the appropriateness of using the simplistic 1.1-approach, but there is no consensus about which model to use instead since there are uncertainties in how exactly RBE depends on the dose, LET, and tissue parameters, etc. Other approaches to consider, to avoid the uncertainties of RBE-models, are LET optimization and track-end optimization, which are using pure physical quantities, to redirect high-RBE protons from OARs to the target(s) or elsewhere.

For carbon ions, the RBE variation is so high throughout the beam that variable RBE-models are needed. Two models are dominating the carbon ions field: the local effect model and the microdosimetric kinetic model. The two different models are used clinically and result in different dose distributions.

In order to estimate the likelihood of curing the disease and the risk of normal tissue toxicity, other radiobiological models, called TCP and NTCP models, are used. They are typically based on follow-up data from cohorts of patients and mathematically describe the relation between dose (potentially combined with several other input parameters) and tumor control or normal tissue toxicity. The clinical use of TCP models is limited, whereas the use of NTCP models is slightly more common in the evaluation of treatment plans. For example, NTCP is suggested to be used in the selection of patient cohort most suitable for proton therapy instead of conventional photon therapy. In order to take advantage of patient cohorts treated with various treatment techniques and different fractionation schedules, the inhomogeneous dose input in TCP and NTCP models can be converted to equivalent uniform distributions (using EUD-models) and corrected for fractionation effects (using EQD-models).

The biological models and their parameter values are subject to large uncertainties which have limited their use in clinical practice. An important cause of the uncertainties is the variability in the experimental data on which the models are based. A general approach to handle uncertainties is scenario-based robust optimization. This technique has been used to mitigate other sources of uncertainty in radiotherapy, including uncertainty in the position of the target relative to the beams, location of cancer cells, organ motion, and patient density data. Then the possible errors resulting from the uncertainties are discretized into different scenarios, each representing a specific configuration for one or several sources of uncertainty.

An optimization problem is then formulated, which includes an objective function and possibly constraints, which describes non-negotiable conditions. The optimization algorithm aims to minimize (or maximize) the objective function while satisfying the constraints. A function used as an objective, as a constituent in an objective, or as a constraint in an optimization problem is denoted "optimization function".

The optimization may, for example, minimize the objective function evaluated in the worst-case scenario, minimize the expected value of the objective function over all scenarios, or use another approach. Alternatively, functions evaluated over the different scenarios may be included as constraints in the optimization. Alternatively, functions evaluated over the different scenarios may be included as constituents in the objective function. Different robust optimization techniques are for example compared and discussed in the articles by Fredriksson, A. (2012). A characterization of robust radiation therapy treatment planning methods—from expected value to worst-case optimization. *Medial Physics*, 39(8), 5169-5181, and Fredriksson, A., and Bokrantz, R. (2014). A critical evaluation of worst-case optimization methods for robust intensity-modulated proton therapy planning. *Medical Physics*, 41. In this way plans less sensitive to errors are obtained as compared to optimization conditioned on only one scenario. One purpose of the present invention is to use the scenario-based robust optimization framework to handle also uncertainties that arise from radiobiological models.

SUMMARY OF INVENTION

An object of the present invention is to provide an improved solution wherein a similar robust optimization approach is provided to handle uncertainties in biological models, where both the uncertainties in model choice and parameter values may be handled simultaneously. This object is achieved in a first aspect of the present invention, in which there is provided a method for generating a robust radiotherapy treatment plan for a volume of a subject, said volume being defined using a plurality of voxels, the method comprising the steps of:

defining an optimization problem using at least one optimization function for a biological endpoint related to the radiotherapy treatment;
  defining a set of scenarios comprising at least a first scenario and a second scenario, wherein at least two of the scenarios in the set of scenarios represent different biological models to quantify the same biological endpoint;
  calculating an optimization function value for each scenario in the set of scenarios;

generating a radiotherapy treatment plan by robustly optimizing the optimization function value evaluated over the set of scenarios.

By adding different radiobiological models and/or different parameter values as different scenarios in a robust optimization setup, treatment plans can be obtained that are robust against both the choice of model and parameter values.

The disclosure proposes performing robust optimization using at least two different biological models, each with different sets of parameter values, as different scenarios so that the goals are obtained as well as possible for all configurations. In this way, the resulting radiotherapy treatment plan is less sensitive to the choice of model and parameter values made but is more robust to errors caused by model and/or parameters inaccuracy. These scenarios could also be combined with others that are defined for uncertainties such as range uncertainties, setup errors, organ motion, etc.

This approach has distinct advantages over the known approach where only physical uncertainties are taken into account, namely to better utilize biological models by explicitly acknowledge the uncertainties involved, and the ability to include combinations of models and parameter values in robust optimization and evaluation.

The plan is to include not only robustness against parameter values but also robustness of model choice. Similar to the possibility today to include e.g. uncertainties in patient setup, densities, and organ motion in robust optimization and evaluation, the idea is to be able to include several biological models each with a range of parameter values to be handled as different scenarios in robust optimization and/or evaluation.

In a preferred embodiment, the biological models quantify biological endpoints comprising equivalent uniform distribution (EUD), equivalent standard fraction doses (EQD), biological equivalent dose (BED), relative biological effectiveness (RBE), RBE-weighted dose, tumor control probability (TCP), normal tissue complication probability (NTCP), complication free cure, secondary cancer, and/or overall survival. According to the disclosure, any model that aims to estimate a biological response following treatment may be used.

In a further preferred embodiment, the optimization problem comprises constraints which define parameters that are maintained during the optimization. The constraints may be e.g. in the form of predetermined doses in a defined sub-volume (e.g. the target), which are not changed during optimization. In this way, the target dose is maintained to ensure a certain dose distribution, but the remaining portions of the radiotherapy treatment plan are robustly optimized.

In an advantageous embodiment, the optimization problem comprises a biological or a physical goal. Preferably, the physical goal comprises dose limits to targets and organs at risk (OAR) in the treatment volume, dose volume histogram (DVH) limits, LET limits, the location where the particles stop and/or homogeneity and conformity indices. In this way, biological uncertainties can also be combined with other (physical) objectives. Plan optimization and evaluation should be able to use different biological models in combination as well as in combination with physical optimization functions and goals.

The optimization problem could be a combination of physical goals such as minimum and maximum doses to targets and organs at risk, respectively, and DVH limits, and biological goals such as EUD, TCP, and NTCP.

In a preferred embodiment, the robust optimization comprises a stochastic programming approach, wherein the expected value of the optimization function is minimized; a minimax approach, wherein the maximum of the optimization function over the error scenarios is minimized; or any combination of the two commonly referred to as minimax stochastic programming; or a voxel-wise worst-case approach, in which the worst case dose to each voxel considered individually is optimized.

In an advantageous embodiment, the set of scenarios further comprises at least a third scenario, wherein the third scenario represents a specific realization of the uncertainty of one or more parameters relevant for treatment planning, comprising particle range, spatial position of the treatment volume, radiotherapy treatment apparatus setup, density of irradiated tissue, interplay effects, organ movement and/or biological model parameter values. In this way, biological uncertainties can also be combined with other uncertainties associated with the parameters relevant for treatment planning.

In an alternative embodiment, the step of generating a radiotherapy treatment plan comprises adapting a pre-existing radiotherapy treatment. In this way, a "warm start" may be achieved by starting from an existing radiotherapy treatment plan in order to arrive at a robustly optimized radiotherapy treatment plan faster and with less computational load compared to the case when starting from zero. The existing radiotherapy treatment plan may be any previously generated radiotherapy treatment plan for the patient (or a standard radiotherapy treatment plan generated using default parameter values automatically obtained).

According to another aspect, there is provided a computer program product comprising computer-readable code means which, when run in a computer, will cause the computer to perform the method according to the first aspect.

According to yet another aspect, there is provided a computer system comprising a processor coupled to a memory having stored thereon computer-readable instructions that, when executed by the processor, cause the processor to perform the method according to the first aspect.

According to an additional aspect, there is provided a treatment planning system comprising a computer system as described above.

BRIEF DESCRIPTION OF DRAWINGS

These and other features, aspects, and advantages of the disclosure will be further explained in the following description with reference to the accompanying drawings, in which.

Herein, identical reference numerals are used, where possible, to designate identical elements that are common to the figures. Also, the images in the drawings are simplified for illustrative purposes and are not necessarily depicted to scale.

DESCRIPTION OF EMBODIMENTS

Figure 1:
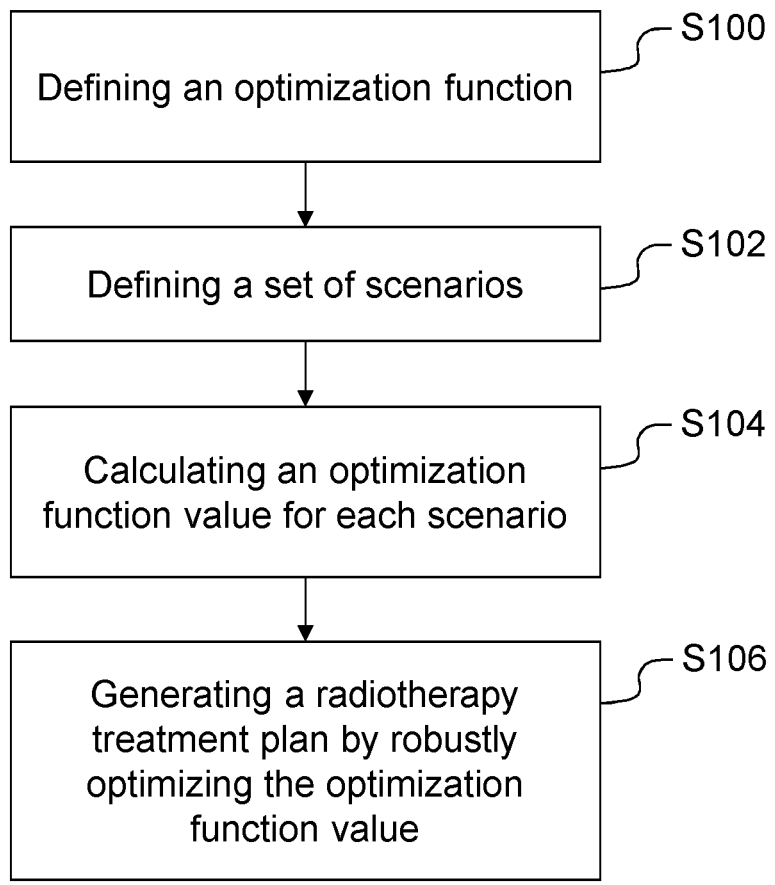
FIG. 1 shows a flow chart representing the steps of a computer-based method for generating a robust radiotherapy treatment plan according to one embodiment of the present disclosure.

FIG. 1 is a flow chart of an embodiment of the method according to the present invention, which may be used in conjunction with generating a radiotherapy treatment plan. In one embodiment the starting point is an initial treatment plan and a number of scenarios to consider, and the method aims to obtain an improved treatment plan based on the initial treatment plan, to modify an initial plan with some constraints, or to obtain a deliverable treatment plan in cases where the initial treatment plan does not satisfy all machine limitations. Depending on the type of data included in the plan, other input data may be needed, for example, data related to the patient, for dose calculation. The initial treatment plan may be obtained in any manner known in the art, including scenario-based and non-scenario-based methods. Typically, it will be a previous plan developed for the same patient (corresponding to a "warm start"), but it could also be automatically obtained from a library of standard plans as mentioned above.

The treatment plan is generated with the purpose of providing radiotherapy treatment of a treatment volume of a subject (patient) which may be an organ and includes a target which may be a tumor or cluster of tumor cells. The treatment volume is defined using a plurality of voxels, as known in the art.

In a first step S100, an optimization function for a biological endpoint related to the radiotherapy treatment is defined. Biological endpoints are quantified based on biological models to estimate the biological effect of radiation, as mentioned above, and may for example comprise maximum and/or minimum limits or goals imposed on one or more of equivalent uniform distribution (EUD), equivalent standard fraction doses (EQD), biological equivalent dose (BED), relative biological effectiveness (RBE), RBE-weighted dose, tumor control probability (TCP), normal tissue complication probability (NTCP), complication free cure, secondary cancer, and/or overall survival.

The optimization function may be included as a constraint in the optimization. Alternatively, the optimization function may be included as an objective function constituent in the optimization. Typically, goals are set for the treatment, and these goals are used to define objective function constituents, constraints or a combination of these. An objective function constituent is a desired goal, towards which the optimization should strive or which the optimization should try to fulfill as well as possible, whereas a constraint is a strict goal or condition that must be satisfied precisely, such as a minimum dose to a tumor or a maximum dose to an OAR or bounds on the variables controlling the objective function.

In general, a first radiobiological objective may be defined using one or more scenarios. For instance, a first scenario may be based on a first radiobiological model and a second scenario may be based on a second radiobiological model. In cases where one or both of the first and second radiobiological models have more than one set of parameter values, each set of parameter values for each radiobiological model may give rise to a different scenario to be used in the method according to the present disclosure. This principle may be further extended using additional radiobiological objectives giving rise to further scenarios based on different radiobiological models and parameter sets, as well as physical goals with one or more scenarios.

As an example, in proton therapy planning one could choose to optimize a treatment plan with the objective to fulfill some defined goals based on RBE-weighted dose using several RBE-models (including the constant RBE-model), each with different sets of parameter values, as different scenarios so that the goals are obtained as well as possible for all configurations. In this way, the plan is less sensitive to the choice of model and parameter values made but is more robust to errors caused by model and/or parameters inaccuracy.

In robust optimization of proton plans, the RBE-weighted dose can then be calculated using both the standard constant RBE model (RBE=1.1) together with e.g. different variable LET-based RBE-models where each model includes a range of parameter values. In this way, the plan will not depend strongly on one model with nominal parameter values but will utilize e.g. worst-case optimization to incorporate uncertainties. This is described more in detail in Example 1 below.

Another example is to use different TCP and NTCP models for the same endpoint, where each model can have different sets of parameter values, together with a set of other models and parameter values for another endpoint. These biological models can be combined with other physical goals. This is described more in detail in Example 2 below.

In step S102, a set of scenarios are defined comprising at least a first scenario and a second scenario. The scenarios represent uncertainties in biological models when quantifying the biological endpoints related to the radiotherapy treatment. The scenarios may be defined manually, or automatically. Several semi-automatic ways of defining scenarios are also perceivable. In a preferred embodiment, the user is allowed to set the magnitudes of the uncertainties as input to the system, which will calculate a suitable set of scenarios based on the uncertainties.

In step S104, an optimization function value is calculated for each scenario in the set of scenarios. In step S106, the optimization function value is robustly optimized, evaluated over the set of scenarios to generate a radiotherapy treatment plan.

Various types of optimization methods for achieving robustness can be used in conjunction with the method according to the present disclosure. For example, minimax (or "composite worst-case") optimization can be used, in which the worst-case scenario over the composite objective function is optimized. The optimization problem is then formulated as $$\min_{x \in X} \max_{s \in S} f(x; s),$$

wherein X is the set of feasible optimization variables (e.g., the set of allowed spot weights, MLC leaf positions, etc.), S is the set of scenarios enumerating the different biological models, and $$f(x;s)$$

is the composite objective as a function of the optimization variables x under scenario s. For example, f (x; s) could be given by g(d(x; s)), where g is a function relating to the dose d(x; s) resulting from the optimization variables x under scenario s. Here, s is a parameter that may completely change the function in question, e.g., f (x; $s_1$) may be the NTCP resulting from a first NTCP model and f (x; $s_2$) may be the NTCP resulting from a second NTCP model, and, similarly, d(x; $s_1$) may be the RBE-weighted dose resulting from a first RBE model, and d(x; $s_2$) may be the RBE-weighted dose resulting from a second RBE model.

Another type of optimization method to achieve robustness is expected value optimization, in which the expected value over the uncertainties is optimized. The optimization problem is formulated as $$\min_{x \in X} Ef(x; Y),$$

wherein E is the expectancy operator and Y is a random variable taking on values from the set S of scenarios.

A third alternative is the voxel-wise worst-case optimization method. In this method, two artificial worst-case dose distributions, $d^{high}$ and $d_{low}$ are calculated. Here, $d^{high}$ is calculated as the highest dose over the scenarios to each voxel considered individually, and $d_{low}$ is calculated as the lowest dose over the scenarios to each voxel considered individually, i.e., $$d_i^{high}(x) = \max_{s \in S} d_i(x; s), i = 1, \ldots, N$$
$$d_i^{low}(x) = \min_{s \in S} d_i(x; s), i = 1, \ldots, N$$

where $d_i$ denotes the dose to voxel i and N is the number of voxels.

The optimization problem is then formulated as $$\min_{x \in X} f^{high}\left(d^{high}(x)\right) + f^{low}\left(d^{low}(x)\right),$$

where $f^{high}$ is a composite objective function with constituents that are used to avoid overdosage (e.g., objectives for the organs at risk, OAR) and $f^{low}$ is a composite objective function with constituents that are used to avoid underdosage (e.g., minimum dose requirements for the target).

Another alternative is to minimize an objective function h(x) not necessarily (but possibly) relating to the full set S of scenarios, and to include constraints for functions f (x; s) for all s in S, i.e., $$\min_{x \in X} h(x) \text{ subject to } f(x; s) \leq 0, s \in S.$$

The objective function h(x) can be formulated in accordance with any of the above methods but can also be formulated to take only the nominal scenario, corresponding to no error, into account.

Other methods, such as the stochastic minimax method, which is a combination of composite worst-case optimization and expected value optimization, can also be used and are known in the art.

Figure 2:
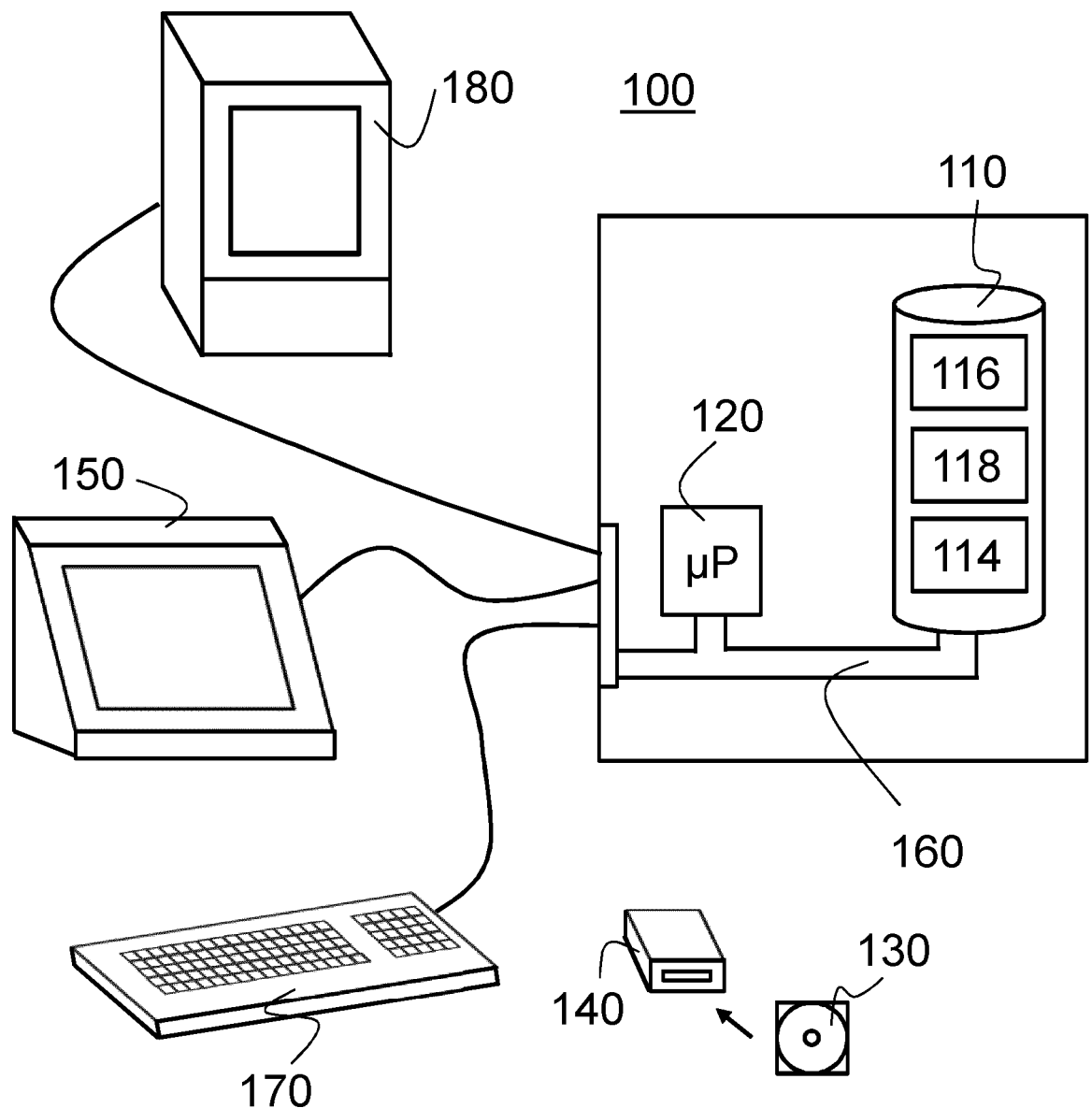
FIG. 2 schematically shows a computer-based system for evaluating, visualizing, generating and improving a radiotherapy treatment plan according to one embodiment of the present disclosure.

Turning now to FIG. 2, it shows a simplified schematic representation of a computer-based system 100 for generating a radiotherapy treatment plan 114, according to the disclosure. The computer-based system 100 includes a memory or database 110 having a radiotherapy treatment plan 114 stored thereon, and a computer program 116 for generating an improved radiotherapy treatment plan 118. Memory 110 can be any volatile or non-volatile memory device such as a flash drive, hard drive, optical drive, dynamic random-access memory (DRAM), static random-access memory (SRAM), and any other suitable device for storing information and later information retrieval and use for data processing. Also, the system 100 includes one or more hardware processors 120 for performing data processing, which are able to access the memory 110. The hardware processor 120 can be made of one or more of a central processing unit (CPU), digital signal processor (DSP), reduced instruction set computer (RISC), application specific integrated circuit (ASIC), complex programmable logic device (CPLD), field-programmable gate arrays (FPGA), parallel processor systems, or a combination of these different hardware processor types.

The computer program 116 is made of computer-readable instructions that can be transferred to hardware processor 120 and can be executed by hardware processor 120. When executed on the hardware processor 120, the computer readable instructions will perform a method for generating an improved radiotherapy treatment plan 118. Results of the processing that is performed by the hardware processor 120 when executing the computer program 116 can be stored in memory 110, for example, the improved radiotherapy treatment plan 118, and associated data. Hardware processor 120 can also access the memory 110 via direct memory access (DMA), and can also use a cache memory for storing temporary processing results. The computer program 116 can also be stored on a non-transitory computer-readable medium 130, for example a universal serial bus (USB) flash drive, optical data carriers such as CD-ROM, DVD-ROM, and Blu-Ray disk, floppy disk, swappable hardware drives, USB external hard drive (HDD), or any other portable information storage device, so that the computer program 116 can be transferred to different computing systems, and also be loaded to the memory 110 of system 100. This can be done by connecting the computer readable medium 130 via a data reader/writer 140 to the system 100, for example, an optical drive, USB interface, etc.

Moreover, the system 100 also includes a display unit 150 that has a display driver that allows visualization of results of the data processing, for example to visualize three-dimensional (3D) representations of a target volume of a patient containing, for example, a tumor or cancer cell, and healthy organs-at-risk for which dose delivery has to be prevented, 3D contour data, or two-dimensional (2D) slice representations for various intersection directions and for LET distribution in both the target volume and for organs-at-risk, biological effect (e.g. probability of injury/cell death/ side effects), etc. For example, a 3D computer reproduction of a CT scan can be displayed. Also, the display unit 150 can display dose volume histogram (DVH) that summarize 3D dose distribution by using a graphical 2D format. For example, the display unit 150 is configured to show comparative DVH diagrams for volumes of the patient showing a dose contribution of the radiotherapy treatment plan 114, and for the same volumes of the optimized or improved radiotherapy treatment plan 118, so that also the LET distribution can be visually compared.

The display unit 150 is used for displaying a 3D scan of the patient that is made prior to the treatment, during the treatment or after the treatment. For example, a 3D computer reproduction of a CT scan can be displayed. Also, the display unit 150 can display LET, dose and/or DVH that summarizes 3D dose distribution by using a graphical 2D format or using a numerical format. For example, the display unit 150 is configured to show comparative LET diagrams for volumes of the patient showing a cancer cell destruction or dose contribution of the radiotherapy treatment plan 114. This is shown and compared for the same volumes of the optimized or improved radiotherapy treatment plan so that the improvement can be visually compared. Also, it is possible that the display unit 150 is equipped with a touch screen functionality and can display a graphical user interface to operate system 100.

In addition, computer system 100 has a system bus 160 that connects the hardware processor 120, memory 110, the data reader 140, touch screen, and various other data input-output interfaces and peripheral devices that are not shown. For example, the computer system 100 can be connected to a keyboard 170 for data input by a user and may be connected to an external radiotherapy treatment planning device 180 that has created the radiotherapy treatment plan, for example, a powerful special-purpose computer. Also, the system 100 may be connected to a CT scanner that is not shown. For example, external device 180 that created the radiotherapy treatment plan 114 may be able to develop a dose and LET distribution calculation algorithm that is coded into software, has access to radiation data on prescribed dose distribution, and machine calibration data, and patient-specific information on the target volume of and organs-at-risk of the patient. This external device 180 can then deliver the radiotherapy treatment plan 114 to computer system 100 for evaluation, visualization, creating a new plan, improving an existing plan taking the LET distribution into account. However, it is also possible that computer program 116 is run on the external device itself, thereby not only generating the radiotherapy treatment plan 114 but also generating the improved radiotherapy treatment plan 118.

Furthermore, a computer program product is introduced for performing parameter optimization. The computer program product 130 comprises computer-readable code means, which when run in the computer carries out the method described above.

Example 1: Robust Biological Optimization for RBE-Weighted Dose

In radiotherapy with charged particles (proton therapy, carbon ion therapy, etc.) one has to account for the relative biological effectiveness (RBE) when prescribing dose to the tumor(s) and risk organs. Instead of using dose, one uses the RBE-weighted dose for this, which is the dose in each voxel multiplied with the local RBE for that voxel. The RBE is, however, a complex function of the microscopic energy deposition characteristics of the particles, the local dose, the tissue characteristics, the biological endpoint of interest, the oxygenation of the tissue, etc. Several models are available to calculate the RBE, and the resulting RBE is highly dependent on the model due to substantial uncertainties in experimental RBE data, and since the models are more or less inspired by biological mechanisms.

Problem: Which RBE model should be used to calculate the RBE-weighted dose?

Suggested solution: Select a minimum of two RBE models and optimize the RBE-weighted dose robustly in order to account for the RBE uncertainties.

Define a new treatment plan or start from a treatment plan pre-optimized using an arbitrary optimization method.
   Define at least one objective for an RBE-weighted dose which one would like to optimize robustly against the uncertainty in the RBE. Examples of such objectives could be:
      Minimum or maximum RBE-weighted dose to the tumor
      Maximum RBE-weighted dose to an OAR
      Maximum average RBE-weighted dose to an OAR
   Optionally, add other objectives or constraints to the composite objective function.
   Select a minimum of two different radiobiological models to calculate the RBE.
   Define a scenario for each selected RBE model, where each scenario then represents a scenario to be used in robust optimization.
   Optimize the treatment plan robustly using the preferred robust optimization framework.

Example 2: Robust Biological Optimization for TCP and/or NTCP

In radiotherapy, the physical quantity of the imparted energy per unit mass, the so-called absorbed dose, is often used as a surrogate for the biological effect. Hence, a radiotherapy plan is often optimized in terms of dose, although the biological effect is the primary quantity of interest.

One could, however, optimize directly on the biological effect via the use of radiobiological models for the tumor control probability (TCP), and the normal tissue complication probability (NTCP). However, there exist several radiobiological models for calculation of the same biological endpoint (TCP or NTCP for a specific biological effect) due to e.g. substantial uncertainties in the clinical data for TCP and NTCP. Moreover, beyond dose, various models also account for the effect of factors such as smoking, diabetes, age, gender, etc.

Problem: Which TCP and/or NTCP model should be used in the biological optimization of a radiotherapy plan?

Suggested solution: Select a minimum of two radiobiological models for the same biological endpoint and optimize robustly in order to account for the biological uncertainties.

Define a new treatment plan or start from a treatment plan pre-optimized using an arbitrary optimization method.
   Define at least one objective based on a radiobiological model. Examples of such objectives could be:
      NTCP for a certain biological endpoint should be minimized or below a certain probability.
      TCP should be maximized or above a certain probability.
   Optionally, add other objectives or constraints to the composite objective function.
   Select a minimum of two different radiobiological models to calculate the TCP and/or NTCP.
   Define a scenario for each selected radiobiological model, where each scenario then represents a scenario to be used in robust optimization.
   Optimize the treatment plan robustly using the preferred robust optimization framework.

Preferred embodiments of a method and system for generating a radiotherapy treatment plan have been disclosed above. However, a person skilled in the art realizes that this can be varied within the scope of the appended claims without departing from the inventive idea.

All the described alternative embodiments above or parts of an embodiment can be freely combined or employed separately from each other without departing from the inventive idea as long as the combination is not contradictory.

The following abbreviations are used:
BED biological equivalent dose
CT computer tomography
CTV clinical tumor volume
DICOM digital imaging and communications in medicine
DVH dose volume histogram
EHR electronic health record system EQD equivalent standard fraction dose
EUD equivalent uniform distribution
eMIX electronic medical information exchange system
GUI graphical user interface
GTV gross tumor volume
HIS hospital information system
HIM health information management system
IMRT intensity-modulated radiotherapy
LET linear energy transfer
MLC multileaf collimator
MRI magnetic resonance imaging system
MU monitor units
NTCP normal tissue complication probability
OAR organ at risk
PBS pencil beam scanning
PET positron emission tomography
PTV planning tumor volume
QA quality assurance
QC quality control
US ultrasonography
RBE relative biological effectiveness
ROI region of interest
RVS record and verify system
SPECT single photon positron emission tomography
TCP tumor control probability

The invention claimed is:

1. A method for generating a robust radiotherapy treatment plan for a treatment volume of a subject, the treatment volume being defined using a plurality of voxels, the method comprising the steps of:
   defining an optimization problem using at least one optimization function for a biological endpoint related to the radiotherapy treatment;
   defining a set of scenarios comprising at least a first scenario and a second scenario, wherein at least two of the scenarios in the set of scenarios represent different biological models to quantify the same biological endpoint;
   calculating an optimization function value for each scenario in the set of scenarios; and
   generating a radiotherapy treatment plan by robustly optimizing the optimization function value evaluated over the set of scenarios.

2. The method according to claim 1, wherein the biological models quantify biological endpoints comprising equivalent uniform distribution (EUD), equivalent standard fraction doses (EQD), biological equivalent dose (BED), relative biological effectiveness (RBE), RBE-weighted dose, tumor control probability (TCP), normal tissue complication probability (NTCP), complication free cure, secondary cancer, and/or overall survival.

3. The claim according to claim 1, wherein the at least one optimization problem comprises constraints which define parameters that are maintained during the optimization.

4. The claim according to claim 1, wherein the at least one optimization problem comprises a biological or a physical goal.

5. The method according to claim 4, wherein the physical goal comprises dose limits to targets and organs at risk (OAR) in the treatment volume, dose volume histogram (DVH) limits, linear energy transfer (LET) limits, the location where the particles stop and/or homogeneity and conformity indices.

6. The method according to claim 1, wherein the robust optimization comprises a stochastic programming approach, wherein the expected value of the objective function is minimized; a minimax approach, wherein the maximum of the objective function over the error scenarios is minimized; or any combination of the two commonly referred to as minimax stochastic programming; or a voxel-wise worst-case approach, in which the worst case dose to each voxel considered individually is optimized.

7. The method according to claim 1, wherein the set of scenarios further comprises at least a third scenario, wherein the third scenario represents a specific realization of the uncertainty of one or more parameters relevant for treatment planning, comprising particle range, spatial position of the treatment volume, radiotherapy treatment apparatus setup, density of irradiated tissue, interplay effects, organ movement and/or biological model parameter values.

8. The method according to claim 1, wherein the step of generating a radiotherapy treatment plan comprises adapting a pre-existing radiotherapy treatment.

9. A non-transitory computer-readable medium comprising computer-readable instructions which, when executed on a computer, causes the computer to perform the method according to claim 1.

10. A computer system comprising a processor coupled to a memory having stored thereon computer-readable instructions that, when executed by the processor, cause the processor to perform the method according to claim 1.

11. A radiotherapy treatment planning system comprising a computer system according to claim 10.

* * * * *